US00PP24198P2

(12) United States Plant Patent
Finn

(10) Patent No.: US PP24,198 P2
(45) Date of Patent: Jan. 28, 2014

(54) RED RASPBERRY PLANT NAMED 'VINTAGE'

(50) Latin Name: ***Rubus idaeus* L.**
Varietal Denomination: Vintage

(75) Inventor: Chad Finn, Corvallis, OR (US)

(73) Assignee: The United States of America, as represented by the Secretary Agriculture, Washington, DC (US)

( * ) Notice: Subject to any disclaimer, the term of this patent is extended or adjusted under 35 U.S.C. 154(b) by 150 days.

(21) Appl. No.: 13/199,578

(22) Filed: Sep. 2, 2011

(51) Int. Cl.
*A01H 5/00* (2006.01)

(52) U.S. Cl.
USPC ..... Plt./204

(58) Field of Classification Search
USPC ..... Plt./204
See application file for complete search history.

*Primary Examiner* — Kent L Bell
(74) *Attorney, Agent, or Firm* — Gail E. Poulos; Lesley M. Shaw; John D. Fado

(57) ABSTRACT

Description and specifications of a new and distinct red raspberry cultivar which originated from seed produced from open pollinated flowers of 'Isabel' (U.S. Plant Pat. No. 9,340) is provided. This new primocane fruiting cultivar can be distinguished by its high yields of large, very bright-red-colored, sweet, flavorful fruit with excellent fresh fruit quality borne on primocanes in late summer.

3 Drawing Sheets

Latin name of the genus and species of the plant claimed: 'Vintage' is a new red raspberry plant that is a *Rubus idaeus* L.

Variety denomination: The new red raspberry plant claimed is of the variety denominated 'Vintage' containing *Rubus idaeus* germplasm.

BACKGROUND OF THE INVENTION

The present invention relates to a new and distinct raspberry cultivar designated 'Vintage' and botanically known as *Rubus idaeus* L. This new raspberry cultivar was discovered in Corvallis, Oreg. in August 2004 and originated from open pollinated seed of 'Isabel' (U.S. Plant Pat. No. 9,340; herein incorporated by reference in its entirety). The new cultivar is larger fruited and the fruit is less firm than its maternal parent. The new cultivar has been asexually reproduced annually since 2004 by the use of root cuttings Corvallis, Oreg. The new cultivar was established in vitro from a cane cutting and microcuttings have been rooted from this sort of culture. The new Raspberry plant has been found to be stable and reproduce true to type through successive asexual propagations.

BRIEF DESCRIPTION OF THE PHOTOGRAPHS

The accompanying color photographs show typical specimen's of the new cultivar at various stages of development as nearly true as it is possible to make in color reproductions.

Figure 1:
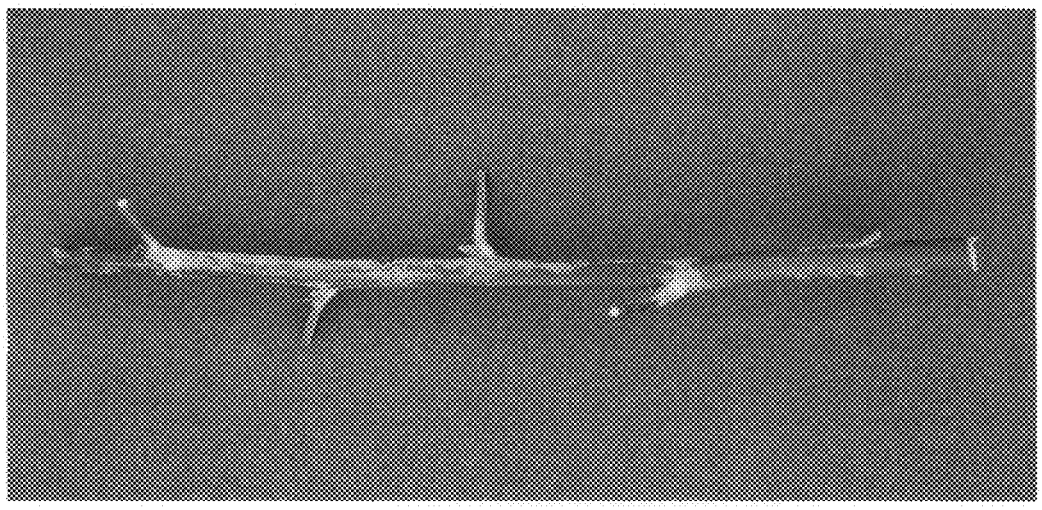

FIG. 1. Shows a section of young cane showing glaucosity and sparseness of prickles.

Figure 2:
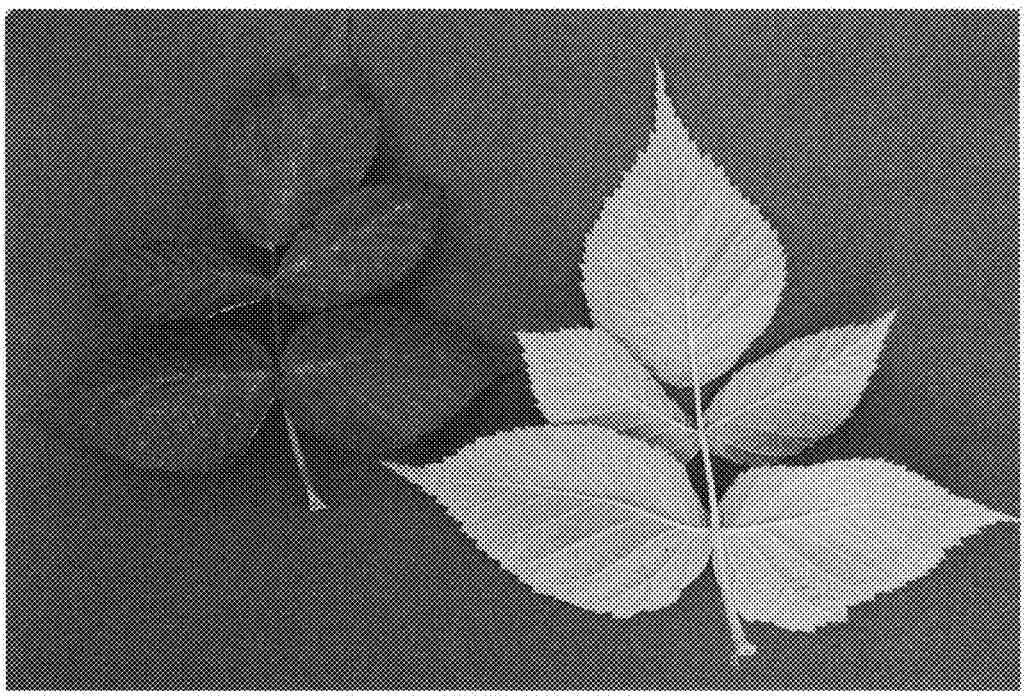

FIG. 2. Shows the upperside and underside of the plant leaves.

Figure 3:
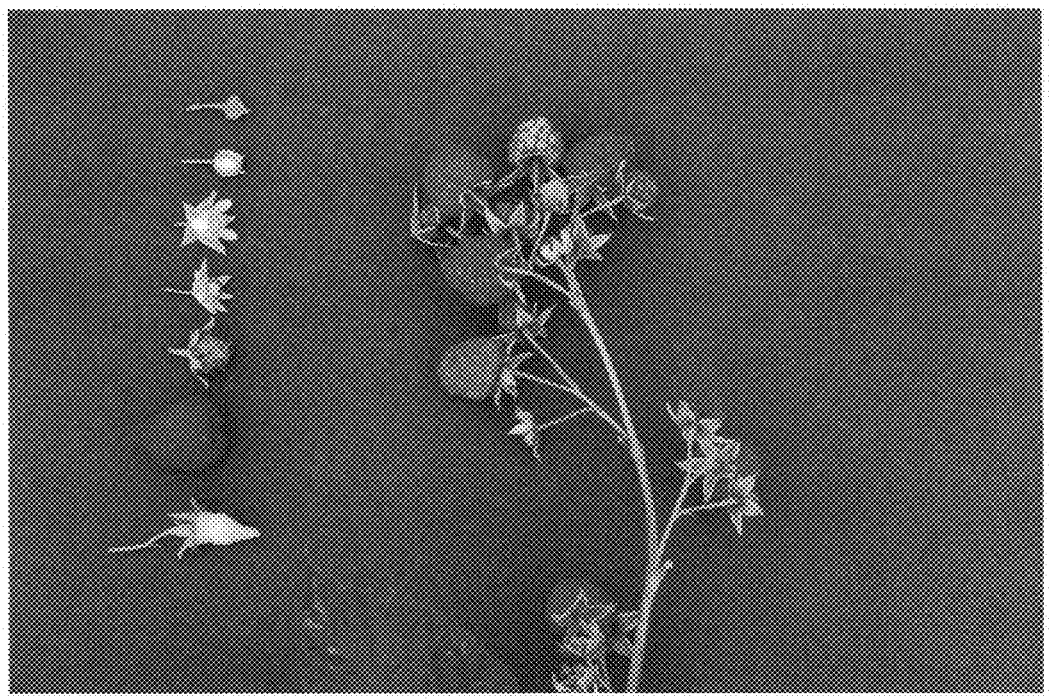

FIG. 3. Shows a range of developmental stages including unopened flower buds, mature open flowers, an immature fruit, a mature fruit without the receptacle, a receptacle with the fruit removed, and a fruiting lateral with ripe fruit.

DETAILED DESCRIPTION OF THE NEW CULTIVAR

The following description of 'Vintage' is based on observations taken from 2006 to 2011 growing seasons in trials in Corvallis and Aurora, Oreg. This description is in accordance with UPOV terminology. Color designations, color descriptions and other phenotypical descriptions may deviate from the stated values and descriptions depending upon variation in environmental, seasonal, climatic and cultural conditions. 'Vintage' has not been observed under all possible environmental conditions. Color terminology follows The Royal Horticultural Society Colour chart. London (R.H.S.) ($5^{th}$ edition, 2007).

TABLE 1

Plant characteristics of the new cultivar compared with plant characteristics of the raspberry plant 'Heritage', (unpatented).

| Characteristic | 'Vintage' | 'Heritage' |
|---|---|---|
| Plant size | Medium | Large |
| Plant diameter/density/vigor | Medium to dense, stocky | Medium to dense, tall, slender |
| Plant height | 1.46 m | 1.77 m |
| Plant width | 0.96 m | 1.00 m |
| Number of canes per hill | 100.33 | 119.00 |

TABLE 2

Primocane characteristics of the new cultivar compared with primocane characteristics of 'Heritage' (unpatented).

| Characteristic | 'Vintage' | 'Heritage' |
|---|---|---|
| New cane habit | Erect | Erect |
| Timing of young shoots emergence from soil | Late | Mid |
| Number of young shoots | Few | Medium |
| Very young shoots intensity of anthocyanin coloration | Weak red, RHS 185B | Weak red, RHS 185B |
| Diameter at 1.2 m from base | 0.76 cm | 0.76 cm |
| Cane cross-section | Round | Round |
| Length at time of fruit formation | 1.63 m | 1.77 m |
| Number of Nodes | 28.33 | 39.33 |
| Internode length-node 2 to 3 from base | 5.33 cm | 6.56 cm |

TABLE 2-continued

Primocane characteristics of the new cultivar compared with primocane characteristics of 'Heritage' (unpatented).

| Characteristic | 'Vintage' | 'Heritage' |
|---|---|---|
| Internode length-midpoint | 5.5 cm | 5.61 cm |
| Internode length-node 5 to 6 from terminus | 5.08 cm | 2.53 cm |
| Cane color | RHS 144D | RHS 144C streaked with RHS 185B |
| Pubescence on canes | Absent | Absent |
| Percent of cane length flowering as primocane | 37.33% | 28.33% |
| Primocane strength: full-grown after picking | Strong | Medium to Strong |
| Glaucosity (waxy bloom) of primocane full-grown after picking | Weak to medium | Weak |

TABLE 3

Floricane characteristics of the new cultivar compared with floricane characteristics of 'Heritage', (unpatented).

| Characteristic | 'Vintage' | 'Heritage' |
|---|---|---|
| Diameter at base | 1.27 cm | 1.08 cm |
| Diameter at 1.2 m from base | 0.74 cm | 0.80 cm |
| Length when dormant | 1.75 m | 2.16 m |
| Number of nodes | 31.17 | 41.17 |
| Internode length (at central ⅓ of cane) | 6.49 cm | 7.36 cm |
| Cane color (dormant) | RHS 175A, RHS 165A, RHS 165B, RHS 165C & RHS 166A with glaucous bloom: RHS 92C, RHS 92D, RHS 85C, & RHS 85D | RHS 165B & RHS 167A & RHS 164A |
| Glaucosity (waxy bloom) | Medium to strong | Absent to weak |

TABLE 4

Prickle characteristics of the new cultivar compared with prickle characteristics of 'Heritage', (unpatented).

| Characteristic | 'Vintage' | 'Heritage' |
|---|---|---|
| Prickles on young shoots | Present | Present |
| Prickle size | Small | Medium |
| Length of prickles (1 m from ground at end of growing season) | 0.77 mm | 1.53 mm |
| Density of prickles--central ⅓ of cane (dense/med/sparse/absent) | Sparse | Medium |
| Prickle texture | Hard, heavy | Hard, sharp |
| Attitude of spine tips | Slightly downward | Downward |
| Prickle shape | Aristate | — |
| Prickle apex | Narrowly acuminate | — |
| Prickle margin | Entire | — |
| Prickle base | Truncate | — |
| Prickle color | Red (RHS 60C) | Dark red (RHS 187B) |

TABLE 5

Primocane leaf characteristics of the new cultivar compared with primocane leaf characteristics of 'Heritage', (unpatented).

| Characteristic | 'Vintage' | 'Heritage' |
|---|---|---|
| Petiole length (range) | 2.56-3.90 cm | 3.20-4.62 cm |
| Petiole length | 3.12 cm | 3.82 cm |

TABLE 5-continued

Primocane leaf characteristics of the new cultivar compared with primocane leaf characteristics of 'Heritage', (unpatented).

| Characteristic | 'Vintage' | 'Heritage' |
|---|---|---|
| Petiole color--upper surface | RHS 144D | RHS 144B |
| Petiole color--lower surface | RHS 149D | RHS 145A |
| Prickle distribution on petioles | Sparse | Medium |
| Rachis length | 45.8 mm | 40.1 mm |
| Rachis length | 1.38 mm | — |
| Rachis diameter | RHS 144B | — |
| Stipule length | 0.55 cm | 0.58 cm |
| Stipule orientation | Erect | Erect |
| Leaf arrangement | Compound, alternate | Compound, alternate |
| Number of leaves per node | One, rarely two | One, sometimes two |
| Entire leaf length | 22.30 cm | — |
| Entire leaf width | 23.87 cm | — |
| Number of leaflets per leaf | Usually three; ranges from one to five | Usually three; ranges from one to five |
| Terminal leaflet length | 9.33 cm | 8.88 cm |
| Terminal leaflet width | 5.75 cm | 6.35 cm |
| Terminal leaflet shape | Oval to ovate | Ovate |
| Terminal leaflet tip/apex | Abruptly or broadly acuminate | Abruptly or broadly acuminate |
| Terminal leaflet base | Cordate | Cordate |
| Terminal leaflet cross section-plane | Convex | Convex |
| Terminal leaflet shape of teeth | Obtuse | Obtuse |
| Terminal leaflet margin | Doubly serrate | Serrate to doubly serrate |
| Terminal leaflet petiolule length | 2.32 cm | 2.41 cm |
| Terminal leaflet petiolule width | 0.17 mm | — |
| Terminal leaflet petiolule color abaxial | RHS 144C | — |
| Terminal leaflet petiolule color adaxial | RHS 145D | — |
| Distal lateral leaflet length | 7.31 cm | 7.80 cm |
| Distal lateral leaflet width | 4.07 cm | 4.36 cm |
| Distal lateral leaflet petiolule length | None, sessile | None, sessile |
| Basal lateral leaflet length | 9.61 cm | 8.89 cm |
| Basal lateral leaflet width | 5.35 cm | 4.45 cm |
| Basal lateral leaflet petiolule length | 0.09 cm | 0.05 cm |
| Color of upper surface of leaflet | RHS 146A to RHS N137A | RHS N137B |
| Color lower surface of leaflet | RHS 191A | RHS 194A to RHS 194B |
| Glossiness | Medium | Medium |

TABLE 6

Floricane leaf characteristics of the new cultivar compared with floricane leaf characteristics of 'Heritage', (unpatented

| Characteristic | 'Vintage' | 'Heritage' |
|---|---|---|
| Number of leaflets | 3 | 3 |
| Petiole length | 6.09 cm | 4.37 cm |
| Stipule length | 6.07 cm | 0.41 cm |
| Terminal leaflet length | 7.87 cm | 7.28 cm |
| Terminal leaflet width | 5.59 cm | 3.83 cm |
| Terminal leaflet petiolule length | 2.49 cm | 1.68 cm |
| Basal lateral leaflet length | 6.52 cm | 6.14 cm |
| Basal lateral leaflet width | 3.62 cm | 2.82 cm |
| Basal lateral leaflet petiolule length | 0.72 cm | 0.11 cm |
| Color of upper surface of leaflet | RHS 146A to RHS 137B | RHS 144A |
| Color lower surface of leaflet | RHS 146A | RHS 148B |

TABLE 7

Flower Characteristics of the new cultivar compared with flower characteristics of 'Heritage' (unpatented).

| Characteristic | Vintage | 'Heritage' |
|---|---|---|
| Bud shape-top view | Pentagonal | — |
| Bud shape-side view | Deltoid with Rounded base | — |
| Bud length | 10.10 mm | — |
| Bud diameter | 9.03 mm | — |
| Bud Color | RHS 144A | — |
| Flower diameter sepal-sepal | 1.82 cm | 1.77 cm |
| Flower diameter petal-petal | 1.60 cm | 1.65 cm |
| Diameter of calyx relative to corolla | 1.44 | 1.08 |
| Flower depth | 8.03 mm | — |
| Number of nodes/lateral (all nodes are flowering Nodes) | 3.17 | 4.17 |
| Number of nodes per lateral with more than One flower | 1.33 | 0.67 |
| Number of buds, flowers, fruit per lateral | 5.50 | 4.17 |
| Number of buds, fowers, fruits per node Of lateral | 1.50 | 1.50 |
| Petal Number | 5.33 | — |
| Petal Length | 6.53 mm | — |
| Petal width | 3.47 mm | — |
| Petal shape | Abruptly acuminate | — |
| Petal apex | Acuminate | — |
| Petal base | Cuneate | — |
| Petal margin | Entire, slightly revolute, undulate near apex | — |
| Color upper and lower surfaces petals | RHS 155B | RHS 155C |
| Sepal number | 5.00 | — |
| Sepal length | 8.47 mm | — |
| Sepal width | 4.33 mm | — |
| Sepal shape | Deltoid | — |
| Sepal apex | Acuminate to aristate | — |
| Sepal margin | Entire and tomentose | — |
| Color inner surface sepals | RHS 145A | — |
| Color outer surface sepals | RHS 144A | RHS 146C |
| Pedicel length | 2.66 cm | 1.27 cm |
| Pedicel diameter | 0.15 cm | — |
| Pedicel texture | Prickly | — |
| Color pedicels | RHS 144B | RHS 146B |
| Stamen number | 73.67 | — |
| Filament color | RHS 155C | — |
| Anther length | 0.63 mm | — |
| Anther width | 0.40 mm | — |
| Anther color-fresh | RHS 158A | — |
| Anther color-dried | RHS 199B | — |
| Pollen color | Clear, colorless | — |
| Pistil number | 86.0 | — |
| Stigma color | RHS 157A | — |
| Stigma shape | Convex, variable | — |
| Style length | 3.23 mm | — |
| Style color | RHS 157B | — |
| Ovary Color | RHS N144D | — |
| Fruiting lateral length-4$^{th}$ lateral from tip | 5.08 cm | 5.10 cm |
| Peduncle length | 22.97 mm | — |

TABLE 7-continued

Flower Characteristics of the new cultivar compared with flower characteristics of 'Heritage' (unpatented).

| Characteristic | Vintage | 'Heritage' |
|---|---|---|
| Peduncle diameter | 1.37 mm | — |
| Peduncle texture | Smooth surface With sparse Prickles | — |
| Peduncle color | RHS 144C | — |

TABLE 8

Primocane fruit characteristics of the new cultivar compared with fruit characteristics of 'Heritage' (unpatented).

| Characteristic | 'Vintage' | 'Heritage' |
|---|---|---|
| Length | 2.01 cm | 1.86 cm |
| Width | 2.01 cm | 1.87 cm |
| Length/width ratio | 1.04 | 1.00 |
| Receptacle length | 1.48 cm | 1.11 cm |
| Receptacle diameter | 0.94 cm | 0.75 cm |
| Drupelet length | 0.55 cm | 0.50 cm |
| Drupelet width | 0.38 cm | 0.34 cm |
| Number of drupelets per fruit | 85.0 | 88.7 |
| Drupelet weight | 39.67 mg | 29.12 mg |
| Individual seed weight | 1.20 mg | 1.27 mg |
| Seed length | 2.47 mm | — |
| Seed width | 1.50 mm | — |
| Seed color (dry) | RHS 165D | — |
| Total seed weight per fruit | 121.52 mg | 1.27 mg |
| Glossiness | Medium | Low |
| Separation from receptacle | Easy | Medium |
| Drupelet cohesion | Medium | High |
| Firmness | Medium | Medium |
| Flavor | Excellent | Mild |
| Fruit color | Bright Red | Dark Red |
| Fruit color-immature | RHS 176B | RHS 180B |
| Fruit color-maturing | RHS 178C | RHS 179A |
| Fruit color-mature | RHS 53A to RHS 53B | RHS 183B |
| Titratable acidity (% as citric acid) | 12.84 | 21.79 |
| Soluble solids (%, in Brix) | 12.21 | 12.19 |
| pH | 3.43 | 3.08 |
| Harvest season | 18 August-15 OCTOBER | 8 SEPTEMBER-15 OCTOBER |
| Length of season | Medium | Medium |
| Yield (actual kg/plant) | 1.90 | 1.72 |
| Productivity | Medium | Medium |

I claim:

1. A new and distinct cultivar of red raspberry plant, substantially as illustrated and described, characterized by its high yields of large, bright-red-colored, sweet, flavorful fruit with excellent fresh fruit quality borne on primocanes in late summer.

* * * * *